United States Patent
Kleinschmidt et al.

(10) Patent No.: US 7,148,341 B2
(45) Date of Patent: Dec. 12, 2006

(54) AAV DNA COMPRISING HELPER VIRUS SEQUENCES

(75) Inventors: Jürgen Kleinschmidt, Bammental (DE); Dirk Grimm, Ludwigshafen (DE); Karola Rittner, Strasbourg (FR)

(73) Assignees: Deutsches Krebsforschungszentrum Stiftung des Öffentlichen Rechts, Heidelberg (DE); Transgene S.A., Cedex (FR)

( * ) Notice: Subject to any disclaimer, the term of this patent is extended or adjusted under 35 U.S.C. 154(b) by 0 days.

(21) Appl. No.: 09/923,270

(22) Filed: Aug. 3, 2001

(65) Prior Publication Data

US 2002/0076801 A1   Jun. 20, 2002

Related U.S. Application Data

(63) Continuation of application No. 09/676,223, filed on Sep. 29, 2000, now abandoned, which is a continuation of application No. 09/297,225, filed as application No. PCT/DE97/02500 on Oct. 24, 1997, now abandoned.

(30) Foreign Application Priority Data

Oct. 25, 1996  (DE)  ................................ 196 44 500

(51) Int. Cl.
*C07H 21/04*  (2006.01)
(52) U.S. Cl. ................. 536/23.72; 424/199.1; 424/233.1; 435/69.1; 435/320.1; 435/456; 435/457; 536/23.1; 536/23.4
(58) Field of Classification Search ........... 424/233.1, 424/199.1; 435/69.1, 285.1, 320.1, 456, 435/457, 465; 536/23.1, 23.4, 23.72
See application file for complete search history.

(56) References Cited

U.S. PATENT DOCUMENTS 5,872,005 A   2/1999  Wang et al. ............. 435/320.1

6,004,797 A   12/1999  Colosi ..................... 435/235.1

FOREIGN PATENT DOCUMENTS

WO   WO 95/06743   3/1995
WO   WO 96/18727   6/1996

OTHER PUBLICATIONS

Bett et al. An efficient and flexible system for construction of adenovirus vectors with insertions or deletions in early regions 1 and 3. Proceedings of the National Academy of Science (1994) vol. 91, pp. 8802-8806.*
Chartier et al., 1996, "Efficient Generation of Recombinant Adenovirus Vectors by Homologous Recombination in *Escherichia coli*," *Journal of Virology* 70(7):4805-4810.
Clark et al., 1995, "Cell Lines for the Production of Recombinant Adeno-Associated Virus," *Human Gene Therapy* 6(10):1329-1341.
Colosi et al., 1995, "AAV Vectors Can Be Efficiently Produced Without Helper Virus," *Blood* 86(10 Suppl. 1):627A.
Fasel et al., 1982, "The region of mouse mammary tumor virus DNA containing the long terminal repeat includes a long coding sequence and signals for hormonally regulated transcription," *EMBO Journal* 1(1):3-7.
Flotte et al., 1995, "An improved system for packaging recombinant adeno-associated virus vectors capable of in vivo transduction," *Gene Therapy* 2(1):29-37.
Laughlin et al., 1983 "Cloning of infectious adeno-associated virus genomes in bacterial plasmids," *Gene* 23(1):65-73.
Stratford-Perricaudet et al., 1992, "Widespread Long-term Gene Transfer to Mouse Skeletal Muscles and Heart," *J. Clin. Invest* 90:626-630.

* cited by examiner

*Primary Examiner*—Ulrike Winkler
(74) *Attorney, Agent, or Firm*—Albert Halluin; Maya Skubatch; Wilson Sonsini Goodrich & Rosati

(57) ABSTRACT

The present invention relates to an AAV DNA having helper virus sequences which are necessary for developing AAV viral particles, a system containing such a DNA and the use of both.

15 Claims, 2 Drawing Sheets

AAV DNA COMPRISING HELPER VIRUS SEQUENCES

This application is a continuation of Ser. No. 09/676,223, filed Sep. 29, 2000, now abandoned, which is a continuation of Ser. No. 09/297,225, filed Apr. 23, 1999, now abandoned, which is a national phase filing of the Application No. PCT/DE97/02500, which was filed with the Patent Corporation Treaty on Oct. 24, 1997, and is entitled to priority of the German Patent Application 196 44 500.0, filed Oct. 25, 1996.

I. FIELD OF THE INVENTION

The present invention relates to AAV DNA having helper virus sequences, a system containing such a DNA and its use.

II. BACKGROUND OF THE INVENTION

AAVs (adeno-associated viruses) are single stranded DNA viruses belonging to the Parvovirus family. For their replication, i.e. for forming viral particles, AAVs require helper viruses, particularly adenoviruses or herpesviruses. In the absence of helper viruses, AAVs may incorporate into the host cell genome, particularly at a specific site of chromosome 19.

The genome of AAVs is linear and has a length of about 4680 nucleotides. It comprises two reading frames which code for a structural gene and a non-structural gene. The structural gene is referred to as cap gene. It is controlled by the P40 promoter and codes for three capsid proteins. The non-structural gene is referred to as rap gene and codes for the Rep proteins Rep 78, Rep 68, Rep 52 and Rep 40. The two former proteins are expressed under the control of the P5 promoter, while the expression of Rep 52 and Rep 40 is controlled by the P19 promoter. The functions of the Rep proteins are represented inter alia by the control of replication and transcription of the AAV genome.

It has now turned out that preparations of recombinant (r)AAV viral particles are frequently contaminated with helper viruses, e.g., adenoviruses or herpesviruses. This contamination considerably limits the use of rAAV viral particles for gene therapy. Efforts made to remove the helper viruses by CsCl density gradient centrifugation or filtration methods have produced little success so far, in particular these methods comprise steps which manifest themselves negatively as regards costs and yield.

Therefore, it is the object of the present invention to provide a product by which rAAV viral particles can be provided without contamination with helper viruses.

III. SUMMARY OF THE INVENTION

The present invention relates to an AAV DNA having helper virus sequences which are necessary for developing AAV viral particles, a system containing such a DNA and the use of both.

IV. BRIEF DESCRIPTION OF THE DRAWINGS

V. DETAILED DESCRIPTION OF THE INVENTION

Figure 1:
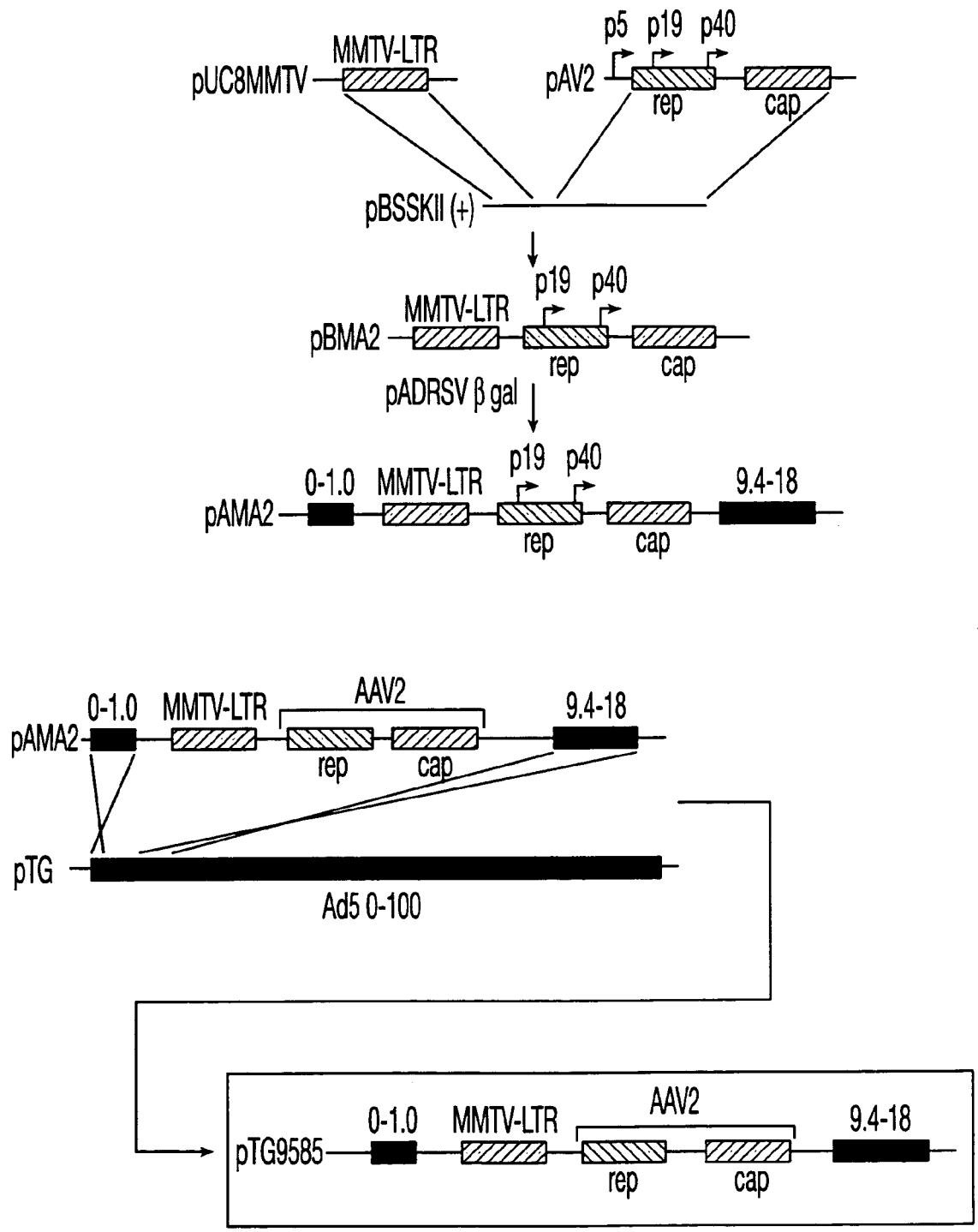
FIG. 1 shows the cloning strategy for obtaining the pTG9585 AAV DNA according to the invention.
Figure 2:
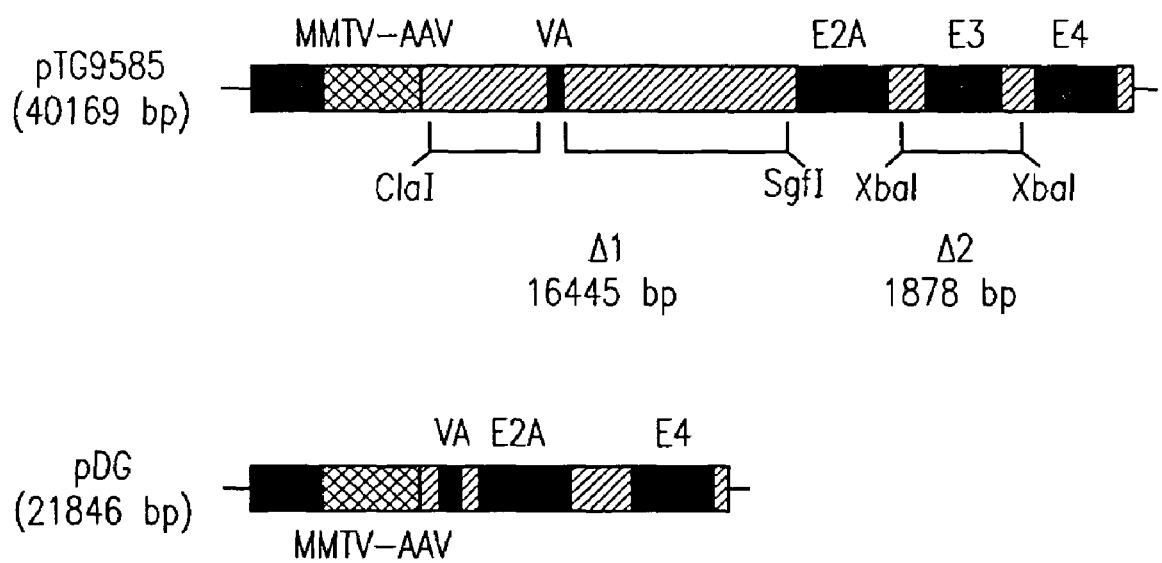
FIG. 2 shows the cloning strategy for obtaining the pDG AAV DNA according to the invention.

It is the object of the present invention to provide a product by which rAAV viral particles can be provided without contamination with helper viruses. According to the invention this is achieved by the subject matters defined in the claims.

Thus, the subject matter of the present invention relates to an AAV DNA having helper virus sequences which are necessary for developing AAV viral particles.

The present invention is based on the applicant's finding that an AAV DNA according to the invention serves for inducing an rAAV vector being present together in the celss with an AAV DNA and containing a foreign DNA to develop rAAV viral particles without having to add helper virus for this purpose.

The expression "AAV DNA" comprises any AAV DNA which may contain helper virus sequences necessary to develop AAV viral particles.

The expression "helper virus sequences" concerns any sequences of a helper virus necessary to develop AAV viral particles. Such sequences originate particularly from herpesviruses and/or adenoviruses, more particularly from adenovirus 5. The sequences may comprise the entire virus genome or fragments thereof.

The expression "rAAV vector" comprises any AAV viral particle and its DNA, which may contain a foreign DNA, except for that of a helper virus, which is necessary to develop AAV viral particles.

With the above exception, the expression "foreign DNA" relates to any DNA which can be incorporated in an AAV vector. The foreign DNA can be non-coding or coding. In the former case, it may be a control element of DNA replication and/or transcription. In the latter case, it is favorable for the foreign DNA to be expressible, it being particularly advantageous for the expression to be controlled by an inducible promoter such as a tissue-specific promoter. In addition, the foreign DNA may code for a diagnostic and/or therapeutic protein. Examples of a therapeutic protein are tumor necrosis factor, plasma proteins and receptors. Moreover, the foreign DNA may be inserted at any site of the AAV vector.

An AAV DNA according to the invention can be prepared by common methods. By way of supplement, reference is made to Sambrook, J. et al., Molecular Cloning, A Laboratory Handbook (Vols. 1–3), Cold spring Habour, New York, (1989). Furthermore, reference is made, in Example 1, to the preparation of the pTG9585 AAV DNA according to the invention. This AAV DNA comprises the complete adenovirus 5 sequence with the exception of the E1 region, as helper virus sequences. PTG9585 is preferred. It was deposited with the DSM [German-type collection of micro-organisms and cell cultures], Braunschweig, as plasmid pTG9585 under number DSM 11248 on Oct. 18, 1996. Also, an AAV DNA according to the invention is preferred which differs from pTG 9585 in that it has a deletion in the structural gene L1 of the adenovirus 5 sequence, particularly in the region of nucleotides 16614–18669. This AAV DNA is referred to as pTG9585 Δ 16614–18669. Besides, an AAV DNA according to the invention is preferred which differs from pTG 9585 in that it comprises two deletions from a total of 18323 base pairs, one deletion relating to great portions of the adenovirus capsid genes and the other deletion relating to the E3 region of adenovirus. This AAV DNA is referred to as pDG and was deposited with the DSM as plasmid pDG under number DSM 11817 on Oct. 15, 1997.

A further subject matter of the present invention relates to a system comprising the above elements, i.e. an AAV DNA, an rAAV vector and optionally a cell. The AAV DNA and/or the cell represent a complementation as regards the AAV sequences of the rAAV vector. The expression "cell" concerns any cell, particularly mammalian cell, which permit the absorption and multiplication of AAV.

By means of the present invention it is possible to provide rAAV viral particle preparations without having to use helper viruses. Therefore, the rAAV viral particle preparations are also free from helper viruses. This is shown particularly when the pDG AAV DNA according to the invention is used. Moreover, the rAAV viral particle preparations distinguish themselves in that they contain no AAV wild-type. They also represent a subject matter of the present invention.

rAAV viral particle preparations according to the invention are perfectly suited for the transduction of cells. It may be favorable for the preparations to be treated with a Dnase prior to their use, so that free AAV DNA is degraded. The cells in consideration are any cells which are present in a body or isolated from a body. Hence it is possible by the present invention to take measures for an ex vivo and in vivo gene therapy.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1

Preparation of the AAV DNA pTG9585 According to the Invention

The cloning strategy for obtaining pTG9585 is shown in FIG. 1. An MMTV LTR fragment from PUC8MMTV (Fasel et al., 1982, *EMBO J.* 1:3–7) is inserted in the multiple cloning site of plasmid pBSSKII(+) (company of Stratagene). Then, 4235 pb of AAV2 sequence from pAV2 (1983, *Gene* 2:65–73) are inserted in this plasmid by means of a synthetic oligonucleotide adapter, which contain the complete rep gene and cap gene as well as the AAV2 promoters p19 and p40. Thus, the AAV2 promoter p5, which controls the expression of the Rep78 proteins and Rep68 proteins, respectively, is replaced in the resulting plasmid pBMA2 by the MMTV promoter. The complete expression cassette consisting of the MMTV-LTR and the AAV2 rep gene and cap gene is then inserted in the vector pAdRSVβgal in the place of the RSV-βgal fragment (J. Clin. Invest. 90, 695–6300. The MMTV-AAV2 fragment is flanked in the thus resulting plasmid pAMA2 on both sides by adenoviral sequences (5': 0–1.0 map units; 3':9.4–18 map units).

By means of homologous recombination (Chartier et al, 1996, *J. Virol.* 70:4805–4810) the MMTV-AAV2 fragment from pAMA2 is inserted in the plasmid pTG3602 (Chartier et al., supra). Thus, the resulting plasmid pTG9585 contains the complete adenovirus 5 sequence, with the exception of the E1 region which is substituted by the MMTV-AAV2 fragment. PTG9585 represents an AAV DNA according to the invention.

B. Example 2

Preparation of the pTG9585 Δ 16614–18669 AAV DNA According to the Invention

A deletion of nucleotides 10983–18670 (the values related to the adenovirus sequence0 is inserted in the AAV DNA pTG9585 prepared in Example 1 by restriction digestion using RsrII. Thereafter, a subfragment including nucleotides 10963–16613 is inserted in the deleted DNA molecule again. Thus, the deletion comprises a range of 2056 bp (nucleotides 16614–18669) from structural gene L1 of adenovirus 5. The pTG9585 Δ 16614–18669 AAV DNA according to the invention is obtained.

C. Example 3

Preparation of the pDG AAV DNA According to the Invention

A deletion of nucleotides 5528–23677 is inserted in the AAV DNA pTG9585 prepared in Example 1 by restriction digestion using ClaI and SgfI. This deletion (18149 base pairs) comprises great portions of the adenovirus 5 capsid gene and the VA region important for the formation of rAAV viral particles. This region (1704 base pairs) is added to the remaining ClaI/SgfI fragment of pTG 9585 again. For this purpose, the VA region of adenovirus 5 is amplified by means of PCR and provided with 5' ends and 3' ends, respectively, which are compatible with ClaI and SgfI, respectively, so that a VA fragment is obtained which can be ligated with the above ClaI/SgfI fragment. An AAV DNA pTG 9585 is obtained which includes a deletion of 16445 base pairs. This AAV DNA is referred to as pTG 9585 Δ 16645.

A further deletion is inserted in pTG 9585 Δ 16445. It relates to the adenovirus 5-E3 region and presents itself as an XbaI fragment comprising 1878 base pairs (30827–32705). For this purpose, pTG 9585 is subjected to BglI digestion and a BglI fragment (27097–37445) which comprises the adenovirus 5-E3 region, is isolated and cloned into pBSSKII (Stratagene). The resulting DNA molecule is subjected to XbaI digestion, so that the above XbaI fragment can be separated. The rest of the DNA molecule is religated and, after BglI digestion, the resulting BglI fragment which is lacking the adenovirus 5-E3 region is inserted in pTG 9585 Δ 16445 by homologous recombination. The pDG AAV DNA according to the invention is obtained.

All references cited within the body of the instant specification are hereby incorporated by reference in their entirety.

What is claimed:

1. A nucleic acid sequence comprising an adeno-associated virus (AAV) nucleic acid sequence, wherein said AAV nucleic acid sequence comprises a rep gene or a cap gene or a rep gene and a cap gene, and an AAV helper virus nucleic acid sequence, wherein said AAV helper virus sequence comprises the complete adenovirus 5 sequence with exception of the E1 region.

2. A nucleic acid sequence comprising an adeno-associated virus (AAV) nucleic acid sequence and an AAV helper virus nucleic acid sequence, wherein said nucleic acid sequence has been deposited with the Deutsche Sammlung von Mikroorganismen und Zeilkulturen under DSMZ 11248.

3. A nucleic acid sequence comprising an adeno-associated virus (AAV) nucleic acid sequence, wherein said AAV nucleic acid sequence comprises a rep gene or a cap gene or a rep gene and a cap gene, and an AAV helper virus nucleic acid sequence, wherein said AAV helper virus nucleic acid sequence comprises the complete adenovirus 5 sequence with exception of L1 and E1 regions.

4. A nucleic acid sequence comprising an adeno-associated virus (AAV) nucleic acid sequence and an AAV helper virus nucleic acid sequence, wherein said nucleic acid sequence has been deposited with the Deutsche Sammlung von Mikroorganismen und Zellkulturen under DSMZ 11817.

5. A composition comprising a nucleic acid sequence of claim 1, 2, 3, or 4, and recombinant adeno-associated virus (rAAV) vector.

6. The composition of claim 5, further comprising a cell.

7. The composition of claim 6, wherein said cell is a mammalian cell.

8. A method for producing adeno-associated viral particle preparation which is not contaminated with helper viruses, comprising:
   a) exposing cells to a nucleic acid sequence comprising an AAV nucleic acid sequence, wherein said AAV nucleic acid sequence comprises a rep gene or a cap gene or a rep gene and a cap gene, and an AAV helper virus nucleic acid sequence, wherein said AAV helper virus nucleic acid sequence comprises the complete adenovirus 5 sequence with exception of the E1 region;
   b) causing said nucleic acid sequence to enter said cells;
   c) inducing said cells to develop said adeno-associated viral particles; and
   d) isolating said adeno-associated viral particles.

9. A method for producing adeno-associated viral particle preparation which is not contaminated with helper viruses, comprising:
   a) exposing cells to a nucleic acid sequence, wherein said nucleic acid sequence has been deposited with the Deutsche Sammlung von Mikroorganismen und Zellkulturen under DSMZ 11248;
   b) causing said nucleic acid sequence to enter said cells;
   c) inducing said cells to develop said adeno-associated viral particles; and
   d) isolating said adeno-associated viral particles.

10. A method for producing adeno-associated viral particle preparation which is not contaminated with helper viruses, comprising:
    a) exposing cells to a nucleic acid sequence comprising an AAV nucleic acid sequence, wherein said AAV nucleic acid sequence comprises a rep gene or a cap gene or a rep gene and a cap gene, and an AAV helper virus nucleic acid sequence, wherein said AAV helper virus nucleic acid sequence comprises the complete adenovirus 5 sequence with exception of L1 and E1 regions;
    b) causing said nucleic acid sequence to enter said cells;
    c) inducing said cells to develop said adeno-associated viral particles; and
    d) isolating said adeno-associated viral particles.

11. A method for producing adeno-associated viral particle preparation which is not contaminated with helper viruses, comprising:
    a) exposing cells to a nucleic acid sequence, wherein said nucleic acid sequence has been deposited with the Deutsche Sammlung von Mikroorganismen und Zellkulturen under DSMZ 11817;
    b) causing said nucleic acid sequence to enter said cells;
    c) inducing said cells to develop said adeno-associated viral particles; and
    d) isolating said adeno-associated viral particles.

12. A method for producing adeno-associated viral particle preparation which is not contaminated with helper viruses, comprising:
    a) exposing cells to a composition comprising (1) a nucleic acid sequence comprising an AAV virus nucleic acid sequence, wherein said AAV nucleic acid sequence comprises a rep gene or a cap gene or a rep gene and a cap gene, and an AAV helper virus nucleic acid sequence, wherein said AAV helper virus nucleic acid sequence comprises the complete adenovirus 5 sequence with exception of E1 region, and (2) an said adeno-associated vector;
    b) causing said composition to enter said cells;
    c) inducing said cells to develop said adeno-associated viral particles; and
    d) isolating said adeno-associated viral particles.

13. A method for producing adeno-associated viral particle preparation which is not contaminated with helper viruses, comprising:
    a) exposing cells to a composition comprising (1) a nucleic acid sequence, wherein said nucleic acid sequence has been deposited with the Deutsche Sammlung von Mikroorganismen und Zeilkulturen under DSMZ 11248 and (2) an said adeno-associated vector;
    b) causing said composition to enter said cells;
    c) inducing said cells to develop said adeno-associated viral particles; and
    d) isolating said adeno-associated viral particles.

14. A method for producing adeno-associated viral particle preparation which is not contaminated with helper viruses, comprising:
    a) exposing cells to a composition comprising (1) a nucleic acid sequence comprising an AAV nucleic acid sequence, wherein said AAV nucleic acid sequence comprises a rep gene or a cap gene or a rep gene and a cap gene, and an AAV helper virus nucleic acid sequence, wherein said AAV helper virus nucleic acid sequence comprises the complete adenovirus 5 sequence with exception of L1 and the E1 regions and (2) an said adeno-associated vector;
    b) causing said composition to enter said cells;
    c) inducing said cells to develop said adeno-associated viral particles; and
    d) isolating said adeno-associated viral particles.

15. A method for producing adeno-associated viral particle preparation which is not contaminated with helper viruses, comprising:
    a) exposing cells to a composition comprising (1) a nucleic acid sequence, wherein said nucleic acid sequence has been deposited with the Deutsche Sammlung von Mikroorganismen und Zeilkulturen under DSMZ 11817 and (2) an said adeno-associated vector;
    b) causing said composition to enter said cells;
    c) inducing said cells to develop said adeno-associated viral particles; and
    d) isolating said adeno-associated viral particles.

* * * * *

UNITED STATES PATENT AND TRADEMARK OFFICE
CERTIFICATE OF CORRECTION

| | | |
|---|---|---|
| PATENT NO. | : 7,148,341 B2 | |
| APPLICATION NO. | : 09/923270 | |
| DATED | : December 12, 2006 | |
| INVENTOR(S) | : Jurgen Kleinschmidt, Dirk Grimm and Karola Rittner | |

It is certified that error appears in the above-identified patent and that said Letters Patent is hereby corrected as shown below:

Column 6, line 17, claim 12, after the number (2), please delete the word "an" and insert the word --a--.

Column 6, line 30, claim 13, after the number (2), please delete the word "an" and insert the word --a--.

Column 6, line 46, claim 14, after the number (2), please delete the word "an" and insert the word --a--.

Signed and Sealed this

Seventeenth Day of April, 2007

JON W. DUDAS
*Director of the United States Patent and Trademark Office*